United States Patent

Shah et al.

[11] Patent Number: 5,932,110
[45] Date of Patent: Aug. 3, 1999

[54] DIALYSATE CONDUCTIVITY ADJUSTMENT IN A BATCH DIALYSATE PREPARATION SYSTEM

[75] Inventors: Dilip H. Shah, Buffalo Grove; Thomas M. Feldsien, Island Lake, both of Ill.

[73] Assignee: Aksys, Ltd., Lincolnshire, Ill.

[21] Appl. No.: 08/762,072

[22] Filed: Dec. 9, 1996

Related U.S. Application Data

[63] Continuation-in-part of application No. 08/388,275, Feb. 13, 1995, Pat. No. 5,591,344.

[51] Int. Cl.[6] .............................. B01D 61/26; B01D 61/28
[52] U.S. Cl. .......................... 210/739; 210/646; 210/647; 210/746; 210/85; 210/143; 210/257.2; 210/321.71
[58] Field of Search ................................ 210/85, 97, 117, 210/143, 252, 258, 257.1, 257.2, 321.71, 321.72, 321.75, 321.84, 321.65, 645, 646, 647, 739, 746

[56] References Cited

U.S. PATENT DOCUMENTS

| | | | |
|---|---|---|---|
| 4,734,198 | 3/1988 | Harm et al. | 210/647 |
| 4,812,239 | 3/1989 | Mills et al. | 210/647 |
| 5,015,389 | 5/1991 | Portillo, Jr. | 210/646 |
| 5,024,756 | 6/1991 | Sternby | 210/93 |
| 5,091,094 | 2/1992 | Veech | 210/647 |
| 5,244,568 | 9/1993 | Lindsay et al. | 210/321.71 |
| 5,247,434 | 9/1993 | Peterson | 210/646 |
| 5,318,750 | 6/1994 | Lascombes | 210/647 |
| 5,336,165 | 8/1994 | Twardowski | 210/646 |
| 5,591,344 | 1/1997 | Kenley et al. | 210/636 |
| 5,616,248 | 4/1997 | Schal | 210/647 |

FOREIGN PATENT DOCUMENTS

| | | |
|---|---|---|
| 2 212 164 | 7/1974 | France . |
| 2 446 075 | 4/1975 | Germany . |
| 8 305 713 | 12/1985 | Germany . |

*Primary Examiner*—John Kim
*Attorney, Agent, or Firm*—McDonnell, Boehnen, Hulbert & Berghoff

[57] ABSTRACT

A method of adjusting the final conductivity of a batch of dialysate to bring the conductivity down to a desired level is described. The batch of dialysate is prepared by mixing excess quantities (e.g., 5%) of dialysate solution chemicals with water to form a solution with a conductivity greater than that required for the particular batch. A measurement of the dialysate solution is taken. A precise volume of water is added to the dialysate solution to dilute the dialysate to the proper level. The precise volume of water is calculated from a known or estimated total system, the desired conductivity level and the actual conductivity. The resulting diluted dialysate is at the desired conductivity level. Excess dialysate which may be present in the dialysate circuit or associated tanks is then flushed to a drain. In a hemodialysis embodiment, the excess dialysate may be flushed through the dialyzer into the blood lines to rinse any pyrogens from the extracorporeal circuit.

5 Claims, 4 Drawing Sheets

DIALYSATE CONDUCTIVITY ADJUSTMENT IN A BATCH DIALYSATE PREPARATION SYSTEM

CROSS-REFERENCE TO RELATED APPLICATION

This continuation-in-part of the prior application of Kenley et al., Ser. No. 08/388,275 filed Feb. 13, 1995, now U.S. Pat. No. 5,591,344, the entire contents of which are incorporated by reference.

BACKGROUND OF THE INVENTION

A. Field of the Invention

This invention relates generally to dialysis machines, including peritoneal and hemodialysis machines, and more particularly to the adjustment of the conductivity of a dialysate solution prepared by the machine so as to insure the proper conductivity of the solution during a dialysis session. The invention is particularly useful in conjunction with a dialysis machine that prepares and stores an entire batch of dialysate solution for the dialysis session, as opposed to dialysis machines based on so-called "proportioning" systems. As used herein, the term "batch" refers to the quantity of dialysate solution that is sufficient for one complete dialysis session for a single patient.

B. Statement of Related Art

Dialysis, including hemodialysis and peritoneal dialysis, is a treatment for patients that suffer from inadequate kidney function. In hemodialysis, blood is pumped from the patient's body through an extracorporeal artificial kidney circuit to a dialyzer. Bloodborne toxins and excess water are filled out of the blood through a semipermeable dialyzer membrane into an electrolyte (dialysate) solution. In peritoneal dialysis, the patient infuses a quantity of dialysate into the peritoneal cavity, and the peritoneal membrane acts as the semipermeable membrane. After a dwell period, the dialysate fluid is drained and a fresh supply of peritoneal dialysate is added to the peritoneal cavity.

Dialysate solution in hemodialysis and peritoneal dialysis machines has typically been prepared using a proportioning technique, wherein a concentrated dialysate solution is mixed with water to form a dialysate solution with the aid of a proportioning pump. To control the dialysate conductivity in a proportioning system, the proportioning pump is precisely regulated, or alternatively, the rate of supply of the dialysate powder and water to a mixing vessel is regulated. A representative dialysis machine that uses precise control of proportioning pumps is described in the Peterson et al. patent, U.S. Pat. No. 5,247,434.

In a batch system, unlike a proportioning system, an entire batch of dialysate (e.g., approximately 50 liters) is prepared shortly before the dialysis session and stored in a dialysate solution tank. In a batch system embodiment of the present invention, dialysate is prepared from a powdered sodium bicarbonate formulation and a liquid acid concentrate that are added to the dialysate solution tank and mixed to water to form an approximately 50 liter batch. The dialysate powder and liquid acid concentrates may be stored in individual containers during shipping, and are opened at the time of preparation of the solution and their contents added to the tank.

Since the total volume of the dialysate tank and associated dialysate fluid circuits is reasonably constant and capable of being determined experimentally, one method of insuring that the concentration and conductivity of the resulting dialysate solution is precisely control the quantity and formulation of the dialysate concentrates that are used to make up each batch of dialysate. This method would work if it were possible to also precisely control the total fluid volume of the dialysate fluid circuit including the dialysate tank.

In practice, the above method has disadvantages. First, precise control of the quantity and formulation of the dialysate concentrates in their individual vessels is difficult and expensive. Additionally, the total fluid volume of the dialysate circuit and tank can vary due to manufacturing tolerances and changes in components over the life cycle of the dialysis machine. If the tank and associated dialysate fluid circuit are subject to heat disinfection cycles, this can cause a slight expansion of the components resulting in an increase in system volume. It has been determined that even small fluctuations in total system volume can cause conductivity measurements that are out of a desired range, unless the quantity of the bicarbonate and liquid acid concentrates added during the preparation of the batch of dialysate are precisely controlled.

The present invention addresses these problems in a novel and unobvious way, and in the process avoids the need for maintaining precise control over (a) the quantities of chemicals in the dialysate vessel used to prepare the solution and (b) the total volume of the dialysis fluid circuit and tank. The invention provides a method of insuring that the conductivity of a batch of dialysate is within a predetermined desired conductivity range. Hence, an object of the invention is to provide a method for effectively controlling the dialysate concentration of a batch of dialysate, insuring that the dialysate concentration and conductivity is at a desired level prior to initiation of dialysis.

SUMMARY OF THE INVENTION

The present invention is directed to a method of providing for control of dialysate conductivity in a batch dialysate system. In accordance with the invention, excess quantities of the sodium bicarbonate and liquid acid concentrates are intentionally added to the dialysate solution tank. Preferably, this technique is practiced by filling vessels containing the sodium bicarbonate formulation and liquid acid concentrates slightly in excess of the target amount, such as by adding 5% extra to the vessels. The dialysate solution is then prepared in the tank acid circulated through the associated dialysate circuit. Since the total average volume of the dialysate tank and associated dialysate circuit flow path can be known (i.e., previously determined experimentally) or at least estimated fairly precisely, and since the desired dialysate concentration and conductivity will also be known, a calculation of the total volume of additional water needed to dilute the dialysate solution down to the proper conductivity and concentration can be made and performed. This amount of water is then introduced into the dialysate circuit and mixed with the dialysate to dilute the dialysate to the desired strength.

The excess dialysate equal to the amount of water introduced into the dialysate circuit) can be flushed from the dialysate flow path if needed, preferably through the arterial and venous lines in the extracorporeal blood circuit and then to a drain, or alternatively directly to a drain. If the excess dialysate is flushed through the extracorporeal circuit (a hemodialysis embodiment), it can additionally serve to flush out any pyrogens and undesizable contaminants that may be present in the extracorporeal circuit.

In a preferred hemodialysis embodiment of the invention, the additional water introduced into the dialysate circuit is supplied first to an ultrafiltration tank placed in communication with the dialysate flow path. During the mixing process, the dialysate solution is circulated through the ultrafiltration tank, thereby mixing the water in the ultrafiltration tank with the dialysate solution, eventually resulting in a thoroughly mixed dialysate solution with the proper conductivity.

The present invention provides for dialysate conductivity control even superior to that achieved with precise pump control in a proportioning system found in the prior art. In the batch system, it is possible to bring the final conductivity very close to the target or desired level. Final conductivity for various formulations for proportioning and batch systems vary from 13 to 15 mS/cm, with ±/−0.6 mS/cm considered acceptable for a proportioning system. However, the method of the present invention can bring the final conductivity level close to ±/−0.2 mS/cm of the target.

Additionally, the invention can be successfully used in a dialysis machine even where small changes in total system volume occur. One possible source of volume changes is the use of a hot water sanitization technique instead of chemical disinfection techniques. The total system volume may deviate slightly from normal due to component expansion after many heat sanitization cycles. Changes in component volumes can also occur as a result of repairs and replacement of components, as well as manufacturing tolerance variations. If the present invention were not utilized in a batch system, the chemical formulation and quantity required in the sodium bicarbonate and liquid acid concentrates will have to increase or decrease fairly precisely. But with the addition of excess chemicals to the tank and later controlled dilution of the solution, as features in the present invention, the formulations can be fixed and such minor variations in system volume can be accommodated, both on a day-to-day basis and over the life of the machine.

BRIEF DESCRIPTION OF THE DRAWINGS

Presently referred embodiments of the invention will be described in conjunction with the drawing figures, in which.

DETAILED DESCRIPTION OF THE PREFERRED EMBODIMENT

Figure 1:
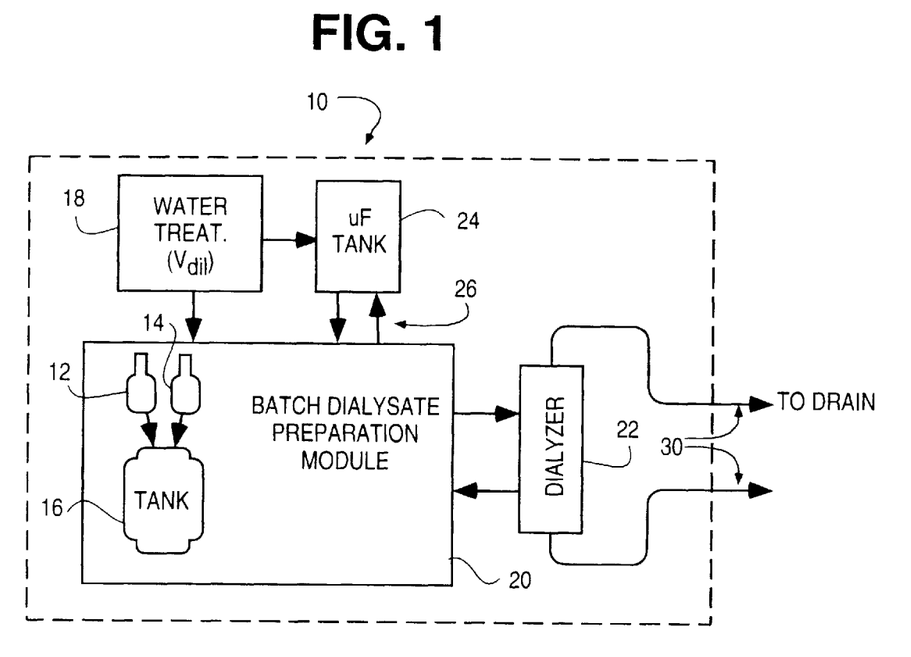
FIG. 1 is a simplified schematic representation showing the structures used to perform the conductivity adjustment method according to a preferred hemodialysis embodiment of the invention.

Referring to FIG. 1, the preferred embodiment of the present invention is used in conjunction with a dialysis machine 10 that prepares a batch of dialysate. To prepare the batch of dialysate, two batch quantity chemical vessels 12, 14 are provided that store a concentrated bicarbonate powder formulation and a liquid acid concentrate, respectively. At the time of preparation of the dialysate, the vessels 12, 14 are opened and their contents dispersed into a dialysate preparation tank 16. The tank 16 is then filled with reverse-osmosis filtered water from a water preparation and treatment module 18 or equivalent supply means. The resulting solution is mixed by circulation in a closed loop in a batch dialysate preparation module 20, for example by swirling action in the tank 16, withdrawal of the solution from the bottom of the tank 16 and reintroduction of the solution into the top of the tank 16.

The total volume of the dialysate fluid circuit path in module 20 including the tank 16 and associated tubing in the dialysate circuit will be known and experimentally determined at the time of manufacture of the machine 10. Given the expected total system volume, a target or desired quantity of dialysate chemicals for the two vessels 12, 14 can be calculated for a solution with a desired conductivity level.

In accordance with the invention, we add approximately 5% excess bicarbonate and liquid acid chemicals to the two vessels 12, 14 (above the desired or target quantity). A suitable range of excess chemicals is presently contemplated at being between about 3% and 7% of normal, depending on the tolerance in the filling of the vessels, the amount of wasted dialysate chemicals one is willing to endure, and other factors. In the examples where the manufacturing variation of the filling of dialysate chemicals in the vessels 12, 14 is +/−5% of the target, the variation will be shifted upwards to a range of between 0% and 10% of the target if 5% excess is added to the vessels. Preferably, the vessels are overfilled such that the resulting conductivity of the batch of dialysate is always at least equal to a target or desired conductivity level.

After the dialysate chemicals are mixed in the tank 16 and circulated through the dialysate flow path in module 20, a dialyzer clearance test is performed. This is performed by circulating dialysate on one side of the dialyzer 22 membrane and circulating water on the blood side of the dialyzer 22. At this time, a separate measurement of the conductivity of the batch dialysate is taken, the quantity $\sigma_{mas}$ in the equations set forth below. Based upon the predetermined average system volume, the measured conductivity, and the desired conductivity of the dialysate, a calculation (described below) is made of the volume of water needed to be added to the dialysate solution to dilute the solution down to the desired conductivity level. This calculation is made by a suitable microprocessor or computer controlling the dialysis machine 10.

In a preferred embodiment, this calculated volume of water is added to an ultrafiltration (UF) tank 24 from the water preparation and treatment module 18 or equivalent supply source. The UF tank 24 is in fluid connection with dialysate solution flow path in the dialysate preparation module 20. The dialysate is pumped through the ultrafiltration tank (represented by arrows 26 in FIG. 1), where it mixes with the water. A period of mixing occurs, for example, 40 minutes, during which time the water in the ultrafiltration tank 24 is thoroughly mixed with the dialysate and the dialysate solution is fully diluted down to the proper conductivity level.

In a volumetrically closed system, such as is the case in the preferred hemodialysis embodiment of the invention, the introduction of additional water into the dialysate flow path must be accompanied by a removal of the same amount of dialysate from the system. In our invention, this can be accomplished by simply pumping a portion of dialysate equal to the volume of introduced water through a valve to a drain. However, the dialysate that is being evacuated from the system can be put to specific purposes, such as rinsing the extracorporeal blood tubing. In a preferred embodiment, we direct the dialysate through the membrane of the dialyzer 22 into the arterial and venous blood tubing set 30. The fluid exits the blood set 30 via a port apparatus connected to the arterial and venous lines (not shown in FIG. 1) and then to drain. In the process, pyrogens or other substances in the arterial and venous lines 30 are flushed from the blood tubing set.

A preferred embodiment of the above technique takes advantage of the storage capacity of the ultrafiltration tank 24. As note above, to dilute the dialysate, the calculated volume of water is added to the ultrafiltration tank 24, and the dialysate solution in the dialysate flow path in module 20 is pumped through the ultrafiltration tank 24, thereby mixing with the water. After a mixing period, e.g., 40 minutes, the dialysate fluid flow path is filled with dialysate and an excess quantity of dialysate is present in the ultrafiltration tank 24. This dialysate is then pumped through the dialyzer 22 and arterial and venous lines 30 and then to drain, and in the process rinsing the arterial and venous lines 30.

In a dialysis machine that is not a volumetrically closed system, such as a peritoneal dialysis machine, the extra dialysate can simply remain in the batch dialysate tank 16, or elsewhere in the flow path.

CALCULATION OF DILUTION VOLUME

The dialysis machine 10 further includes a host central processing unit or computer (not shown in the drawings) that governs operation of the machine, such as the host CPU described in the above-cited Kenley et al. patent, U.S. Pat. No. 5,591,344. A central computer control of a dialysis machine is well known in the art. The host CPU calculates the volume of water needed to dilute the dialysate solution. The equation for volume dilution is derived from the following relationship:

$$\sigma = aI + b \quad (1)$$

where σ=conductivity in mS/cm
I=total ionic strength in mEq/l
a=coefficient of linearity
b=constant of linearity, determined experimentally for a particular dialysate formulation.

This equation (1) is found to work within a 10% range of the desired concentration for any specific dialysate formulation. The regression coefficient is better than 99.9%. Also, when a higher concentration of dialysate is diluted to lower concentration by addition of RO water which has very low conductivity (less than 0.1 mS/cm), the resulting solution has all of its constituents proportionally lowered in equal percentages.

Each dialysate formulation conductivity can be experimentally and theoretically derived and will be termed "desired conductivity, $\sigma_{des}$." Similarly, $I_{des}$ is the desired ionic strength. Applying equation (1) to the desired formulation we get, $$\sigma_{des} = aI_{des} + b \quad (2)$$

Applying equation (1) to a measured bulk formulation before dilution we get, $$\sigma_{mas} = aI_{mas} + b \quad (3)$$

The quantity $\sigma_{mas}$ will vary from batch to batch after dilution with water due to the varying quantity of chemicals in the vessels 12, 14, and is measured by a conductivity cell in the dialysate flow path after the dialysate solution is mixed. Also, overall mass balance applied to the total dialysate fluid system yields the following result:

$$V_{sys} \cdot I_{mas} = (V_{sys} + V_{dil}) I_{des} \quad (4)$$

where $V_{sys}$=Total system volume (without UF tank)
$V_{dil}$=Volume for dilution to be added to the dialysate (e.g., added to UF tank 24) Solving equations (2), (3) and (4) for dilution volume yields, $$V_{dil} = (V_{sys})(\sigma_{mas} - \sigma_{des})/(\sigma_{des} - b) \quad (5)$$

Thus, equation (5) gives the total volume of water needed to dilute the batch of dialysate to the desired conducting level. A variant on the above method is to account for the conductivity of the RO water used for dilution, $V_{dil}$. Although the RO water ($V_{dil}$) can contributed up to 0.1 mS/cm, its effect on 13–15 mS/cm fluid is 100 times less. Also, the impact of lesser concentration on conductivity is much higher, reducing the impact to 200 to 300 times less. Thus, accounting for RO conductivity in $V_{dil}$ in (5) would only need to perform where extraordinarily precise control of conductivity is required, and where the properties of the local water supply are known in advance. Also, in the preferred embodiment the conductivity cell measuring conductivity of the dialysate has an accuracy of ±/–% and the accuracy of volume measurement in the UF tank 24 may be ±1%. The worst case accuracy for dilution volume is estimated at 2 to 3%. If mixing is complete, this method can still achieve 1% accuracy on the desired conductivity. Greater accuracy of the quantity of water added to the dialysate solution flow path can be achieved by using a flow meter in the water line, or other suitable method if necessary, rather than measuring the volume in the UF tank 24. An accuracy of dialysate conductivity to within 1% of the desired or target level, as achieved by present invention, is a substantial improvement over the 5% guideline set forth by the AAMI (Association for the Advancement of Medical Instrumentation).

It will be further understood that an entire suite or collection of dialysate formulations may be required for preparation of difference dialysate solutions to treat a given dialysis patient population. The collection of vessels for the liquid acid and bicarbonate formulations will accordingly have varying amounts and compositions to form the basis for the suite of formulations. The invention is preferably practiced by adding excess chemicals (e.g., 5%) to each of the individual liquid acid and bicarbonate formulation vessels, and following the above dilution procedure for every formulation when the solution is prepared.

Figure 2:
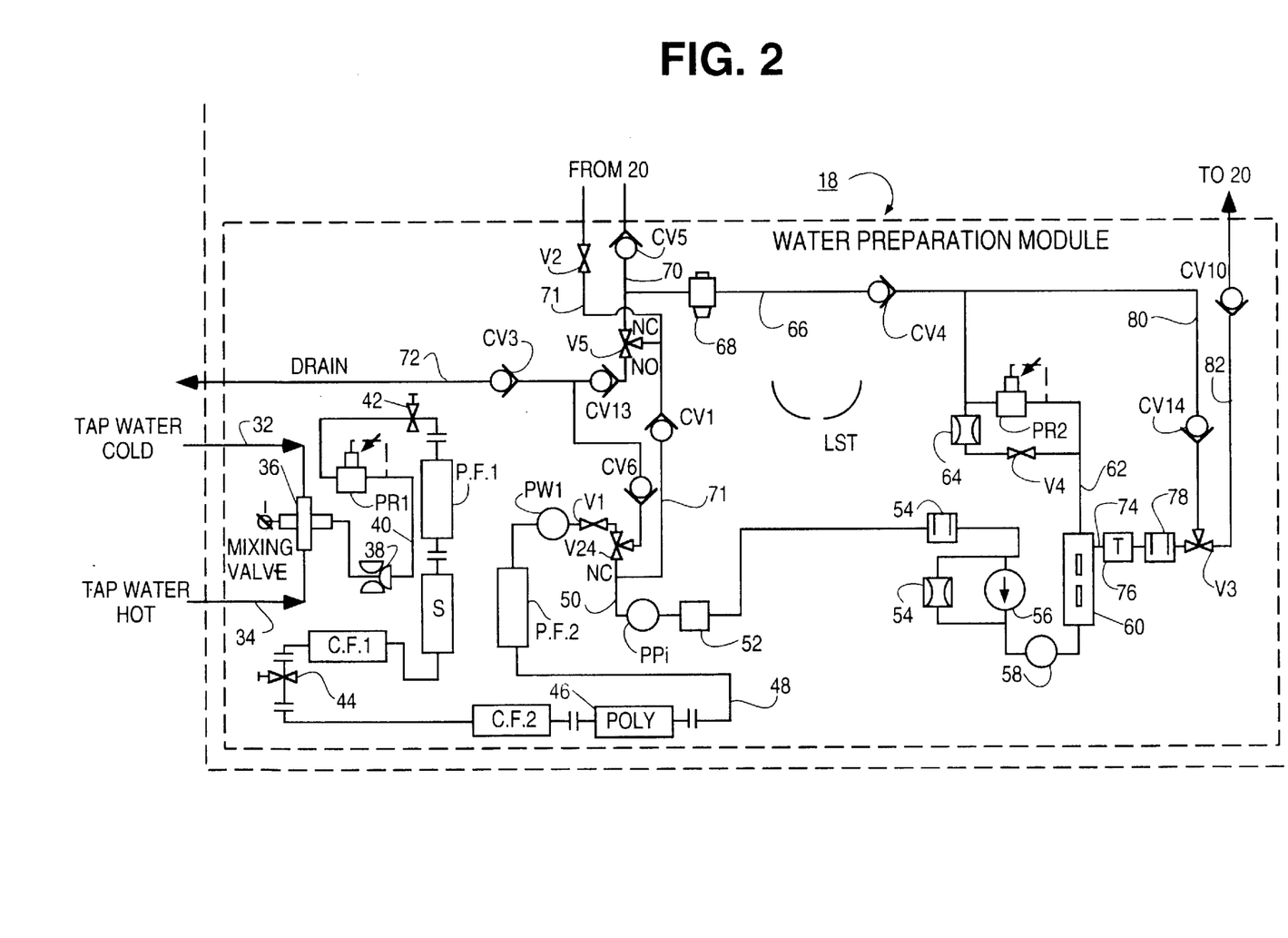
FIG. 2 is a more detailed schematic diagram of a water filtration module used to supply the dilution volume to the dialysate preparation module of FIG. 1, and FIGS. 3A and 3B are more detailed schematic diagrams of a presently preferred batch dialysate preparation module and extracorporeal circuit module of FIG. 1 for use in performing the invention in a hemodialysis machine.
Figure 3A:
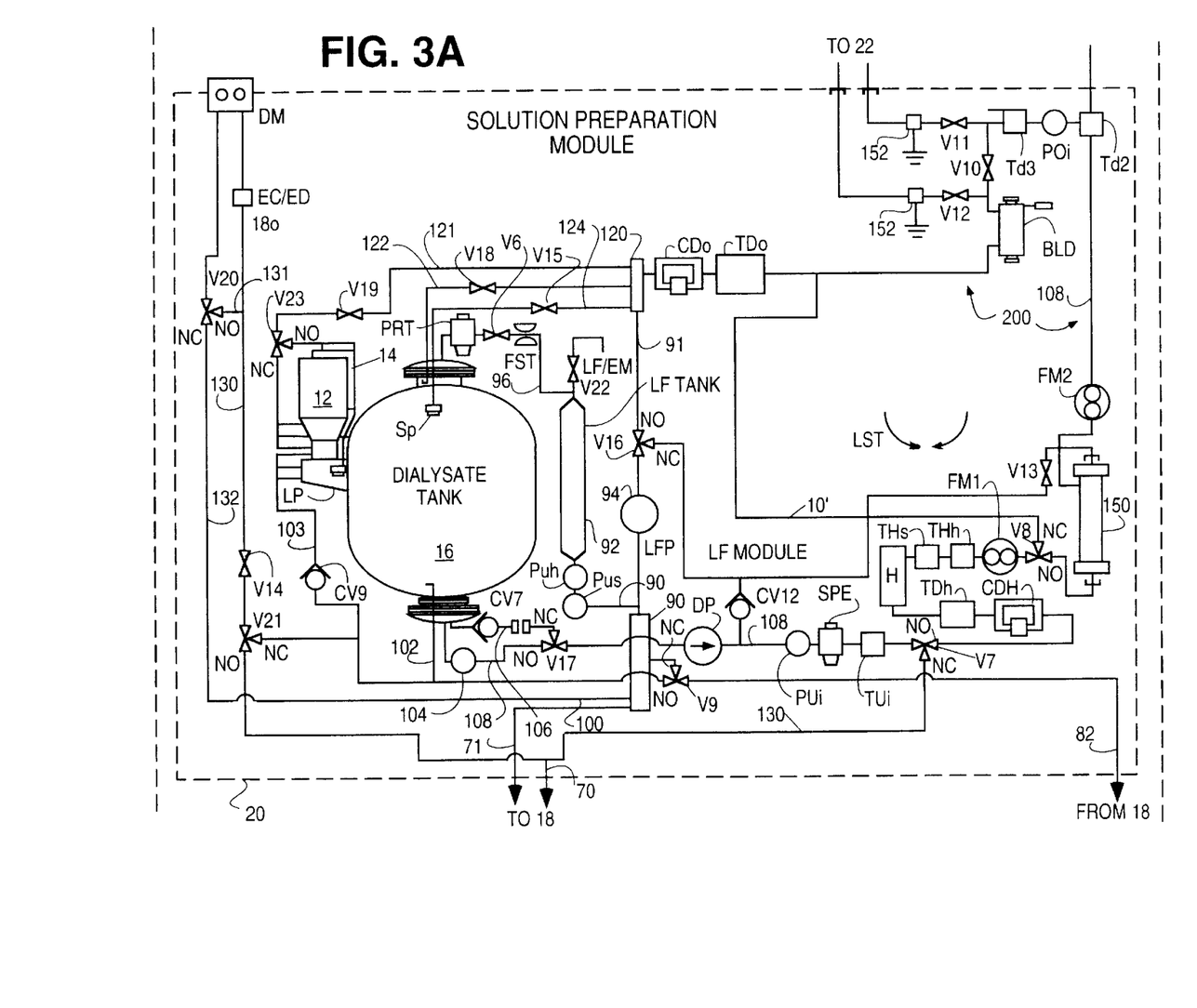
Figure 3B:
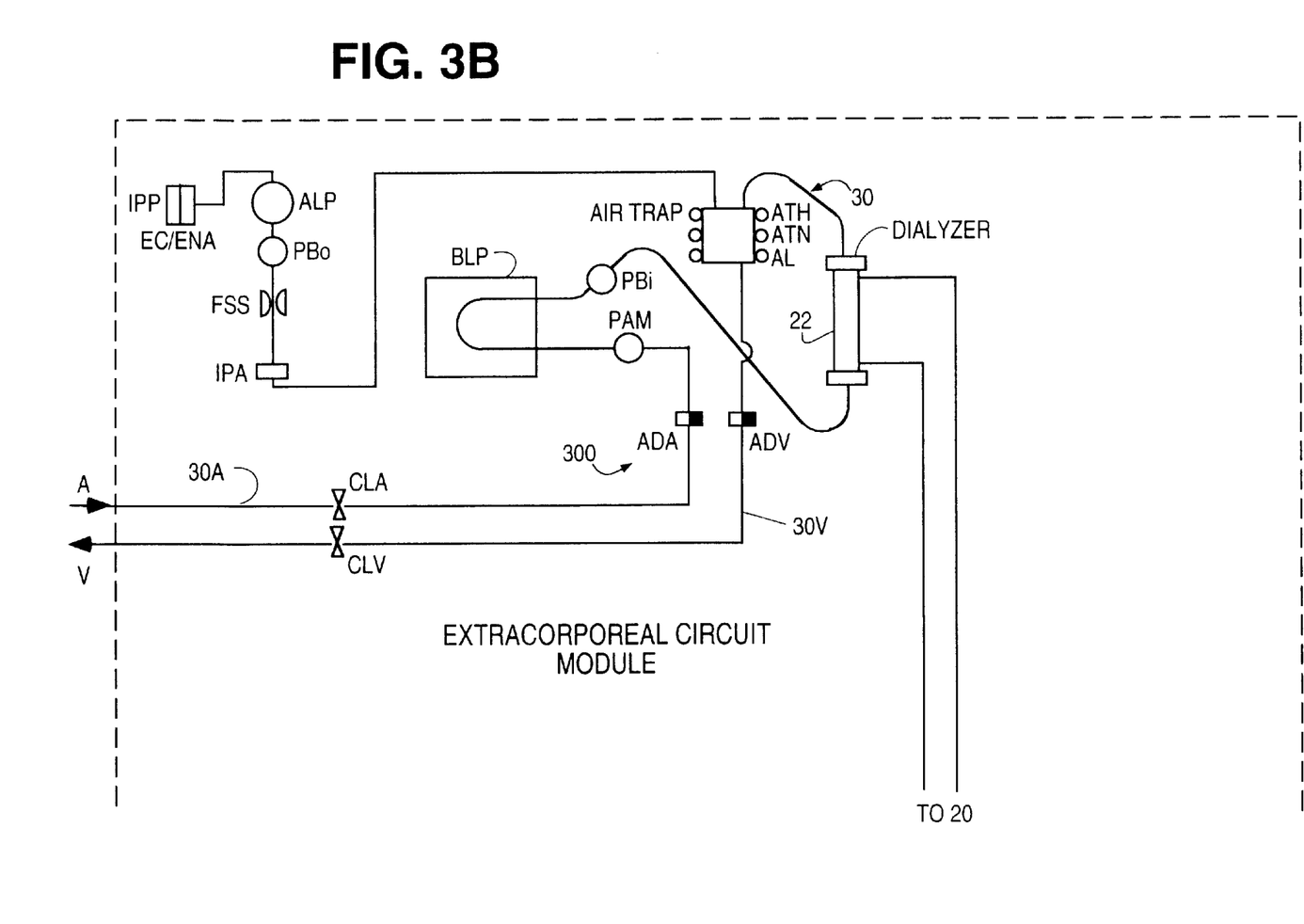

Detailed schematics of a preferred hemodialysis embodiment of the invention are shown in FIGS. 2 and 3. FIG. 2 shows schematically a preferred water preparation module 18 that prepares filtered water for the dialysis machine from incoming tap water, and supplies the water to the dialysate preparation module 20, shown in detail in FIG. 3.

Referring to FIG. 2, cold tap water is applied on a line 32 to a temperature controlled mixing valve 36, where it is mixed with hot water supplied on a line 34. The temperature controlled mixing valve 36 supplies water at a desired temperature (e.g., 30 degrees C.) to the rest of the fluid circuitry. This circuitry includes a back flow preventer 38 in an inlet line 40, a pressure valve PR1, a shut off valve 42, a primary particulate filter PF1, an optional water softener S, and a primary carbon filter CF1. A valve 44 with a sample removal port is provided in the line 40. A secondary carbon filter CF2, a polyphosphate water conditioning and surfactant agent 46 and a secondary particulate filter PF2 are provided in line 48, which supplies water past water inlet pressure transducer PW1. Electrically activated valves V1 and V24 are placed in the inlet line 48. The normally closed port NC of valve V24 leads to a line 50 having a pressure sensor PPi, a thermistor 52, and an invasive conductivity cell 54, which supplies water to a pump 56. A flow constrictor 54 is placed across the inlet and outlet of the pump 56. The outlet line from pump 56 includes a pressure transducer PRi 68 which measures the pressure on the inlet of a Reverse Osmosis (RO) filter 60.

The feed side of the RO filter 60 includes a line 74 having a thermistor 76, a second invasive conductivity cell 78, a three-way valve V3 and an outlet line 82 supplying water to the dialysate preparation module 20. The reject side of the RO filter includes a line 62 having a valve V4, a flow constrictor 64, and a pressure regulator PR2. The line 62 and line 80 from valve V3 lead to a drain line 66 having a check valve CV4 and a pressure relief valve 68 with integral sample removal port 68. The drain line 66 meets with a drain line 70 from the dialysate preparation module 20 and leads to three way valve V5. This line continues with a check valve CV 13, a second check valve CV 3 and leads to a drain line 72 leading out of the dialysis machine 10. Line 71 also leads to the water preparation module 19 via valve V2 and provides for introduction of hot water through lines 50, 74, 62, 80, 82 and 66 during hot water sanitization periods for the water preparation module 18.

It will thus be appreciated from FIG. 2 that incoming water on line 32 and 34 is treated for chlorine or chloramine by the carbon filters CF1 and CF2, treated for particulate matter by the particulate filter PF1, conditioned by the polyphosphate cartridge 46, and reverse osmosis filtered by RO filter 60. The feed water is supplied via line 82 to the batch dialysate preparation apparatus and the ultrafiltration tank in a dialysate preparation module 20 in a manner described in detail below.

FIG. 3 shows a presently preferred dialysate preparation module 20 in a detailed schematic diagram. Inlet RO filtered water on line 82 is supplied to a three way valve V9. The normally closed port NC on valve V9 leads to a line 90 supplying water to an ultrafiltration tank 92 (the same as UF tank 24 in FIG. 1). Two pressure sensors PUS and PUH measure the hydrostatic pressure and hence volume of fluid in the UF tank 92. A UF pump 94 pumps dialysate from the dialysate circuit via V16 into the UF tank to assist in mixing dialysate with water in the UF tank 92 as described above. The top of the UF tank is connected via line 96, a valve V6, and a pressure relieve valve PRT to the top of a dialysate preparation tank 16.

The dialysate preparation tank 16 receives the incoming RO water through valve V9 and inlet lines 100 and 102 at the bottom of the tank 16. A pair of batch dialysate chemicals vessels 12 and 14 and a loading platform LP are positioned against the side of the tank 16. A preferred loading platform apparatus LP, and the process and structures for automatically opening the vessels 12, 14 and adding the dialysate chemicals to the tank 16, and the process of mixing the batch of dialysate in the tank 16, are described at length in the above-referenced Kenley et al. U.S. Pat. No. 5,591,344.

The dialysate circuit 200 flow path includes outlet lines 108 and 106 from the bottom of the tank 16 which lead to three way valve V17. Line 106 is a degrassing line. Line 108 has a pressure transducer 104 for measuring the volume of fluid in the tank 16. The valve V17 leads to a dialysate pump DP which pumps the dialysate from the tank 16 to the dialyzer 22 and back to the tank 16. In the dialysate line 108, the following components are placed in the fluid path:

PUi—a pressure transducer;
SPt—a sample removal port for allowing samples of fluid to be removed from the line 108;
TUi—a thermistor;
V7—a three-way valve connecting line 108 to line 130;
CDH—a noninvasive conductivity sensor for measuring the conductivity of dialysate in line 108, and sending readings to a host central processor;
TDH—a thermistor sending temperature readings to the host CPU, enabling temperature compensation for the conductivity readings;
H—a heater for heating the dialysate to the proper temperature, and water to a high level disinfection temperature during disinfection cycles of the machine;
THs and THh—thermistors sending temperature readings to safety (backup) and host CPUs
FM1—a flow meter
V8—a three-way valve connecting line 108 with line 101.

A pyrogen filter 150 is placed in the dialysate line 108 to filter any pyrogens in the dialysate. A flow meter FM2 measures the flow rate of dialysate to the dialyzer 22. Thermistors Td2 and Td3 measure the dialysate temperature prior to entering the dialyzer 22. Pressure sensor Pdi measures the inlet dialysate pressure. Valves V10, V11, and V12 control the flow of dialysate into and out of the dialyzer 22. V11 is a bypass valve, and closes and V10 opens to divert dialysate away from the dialyzer. V12 closes to force dialysate through the dialyzer 22 membrane into the extracorporeal circuit 300. Ground contacts 152 electrically ground the dialyzer 22, isolating the patent's blood from any stray currents in the dialysate circuit. A blood leak detector BLD detects the presence of blood in the dialysate line 110 containing "old" dialysate. A dialysate temperate thermistor Tdo and a conductivity cell Cdo operate together to measure conductivity of the dialysate in the line 110.

The dialysate coming back from the dialyzer 22 in line 110 meets a manifold 120. Ordinarily, during dialysis, dialysate passes on line 122 past valve V18 into the top of the tank 16. During mixing, dialysate passes through line 124 having valve V15 and into a sprayer SP suspended within the tank 16. During dialysis, a specified quantity of dialysate and fluid from the patient is removed from the line 110 into a line 91 past valve V16 by the ultrafiltration pump 94 and pumped into the UF tank 92 in accordance with the ultrafiltration principles taught in the above-referenced Kenley et al. Patent, U.S. Pat. No. 5,591,344. A fourth line 121 is used to direct fluid (or water) via valve V19 to a three way valve V23, which supplies water to the opening apparatus below the vessels 12 and 14. The normally open port of valve V23 leads to the sprayer within the loading platform LP. A drain line 103 drains fluid from the opening apparatus and conducts it to the drain line 70 via valve V21.

The operation of valves V9, V16 and the operation of the ultrafiltration pump 24 also can cause fluid from the ultrafiltration tank 92 to be pumped along a line 132 past valve V20 to a disinfection manifold DM. The disinfection manifold DM has two ports that receive the connectors at the end of the patient's arterial and venous lines after treatment. Line 132 supplies fluid to the arterial line 30A when the arterial line is connected to its port. Line 130 receives fluid from the venous line 30V when the venous lines 30V is connected to its port. Valve V14 and valve V20 provide a way for recirculating fluid through the arterial and venous lines 30A and 30B when the blood pump BLP of the extracorporeal circuit 300 is operative and the lines 30 are connected to their respective ports in the manifold DM. Line 130 is connected via a valve V21 to the drain line 70 of the water preparation module 18.

The reader is directed to the disclosure of the above-referenced Kenley et al. patent U.S. Pat. No. 5,591,344 for a more exhaustive discussion of the components and operation of the dialysate preparation module 20. The minor differences between the circuitry of FIG. 3 and the dialysate preparation module of the Kenley et al. patent are irrelevant for the purposes of describing the present dialysate conductivity adjustment invention. Similarly, a discussion of the various components of the extracorporeal blood circuit 300 are more fully set forth in the Kenley et al. patent, and will be omitted here since such details do not pertain to the present invention.

Referring now to the particular embodiment of FIGS. 2 and 3, excess dialysate chemicals are added to the chemical vessels 12 and 14 as described above. To prepare the dialysate, the contents of the vessels 12, 14 are added to the tank 16 via the loading platform LP. The tank 16 is supplied with RO water via line 82, valve V9 and inlet line 102. The dialysate is mixed by circulation through lines 108, 110 and manifold 120, and reintroduced into the tank 16 via sprayer SP and line 124 and/or line 122.

After mixing, a conductivity measurement of the resulting dialysate is performed by conductivity sensor CDH. In a preferred embodiment, this measurement is taken during a dialyzer clearance test, in which RO water is sent from module 18 via line 82, valve V9 and line 132 into the arterial line 30A and circulated single pass through the dialyzer 22 and out venous line 30V via line 130 to drain line 70. Dialysate is circulated through the dialyzer 22 and returned in line 110 to the top of the tank 16. The calculation, described above, of the quantity of water $V_{dil}$ needed to dilute the dialysate to the desired conductivity is then performed. The UF tank 92 is initially empty. This dilution volume per equation (5) is added to the UF tank 92 from the water preparation module via valve V9 and line 90.

Next, the dialysate in the tank 16 is mixed with the water in the UF tank 92. Dialysate is pumped by the UF pump 94 from line 91 through valve V16, through the UF tank 92 and out of the top of the UF tank 92 through line 96 and into the dialysate tank 16. The water/dialysate solution in the extracorporeal circuit is circulated in a closed loop though valve V20 with valve V14 closed. After mixing a period of 40 minutes, the system conductivity is measured with conductivity cell CDO in the dialysate line 110 to confirm that the conductivity of the dialysate is at the expected level.

The excess volume of dialysate created by the addition of the dilution volume added to the circuit is present in the UF tank 92 at the end of the mixing period. This fluid is then preferably removed, such as by directing the dialysate to a drain. In one embodiment, valves V7 and V21 are operated such that dialysate is removed from the UF and 92 through valve V7, into line 130 and into the drain line 70.

In a preferred embodiment, the dialysate is flushed through the dialyzer 22 and blood set 30. This is achieved by closing valves V10 and V12, and operating the dialysate pump DP to force dialysate through the dialyzer 22 and into the blood set 30. Valve V20 is placed into a condition such that line 132 is closed off but the line 131 connecting line 132 to line 130 is open. The dialysate is flushed from the arterial and venous lines 30A and 30V out the line 130, through valve V14, and through drain line 70 to the drain of the machine shown in FIG. 2. In a less preferred embodiment, the dialysate could be pumped through the ports of the disinfection manifold DM via line 132, circulated through the arterial and venous lines, and flushed to drain via lines 130 and 70. This technique would only be performed if the dialysate had been first passed through a pyrogen filter (such as the pyrogen filter 150) prior to entry of the dialysate into the blood lines 30, in order to avoid introducing any pyrogens into the blood lines.

In an alternative embodiment, the volume of water $V_{dil}$ is added to the dialysate solution tank 16 and mixed with the dialysate solution stored in the tank 16.

Many specific details concerning the operation of the mixing of the dialysate solution, the construction of the opening apparatus for the dialysate chemical vessels, and other aspects of the embodiment of FIGS. 2 and 3 will be apparent from the above-referenced Kenley et al. U.S. Pat. No. 5,591,344. Presently preferred constructions of the bottles 12, 14 are described in the patent application of Dilip H. Shah et al., Ser. No. 08/660,694, filed Jun. 5, 1996, now U.S. Pat. No. 5,788,099, which is incorporated by reference herein. Presently preferred dialysate chemical formulations are described in the patent application of Dilip H. Shah et al., Ser. No. 08/712,424, filed Sep. 11, 1996, also incorporated by reference herein.

Further, the present invention may be practiced in batch dialysate preparation systems that vary in terms of their fluid circuitry components and design from the embodiment described herein. The true scope and spirit of the invention is intended to encompass these types of modifications from the details of the presently preferred embodiments. Further, the term "module" is intended to refer to a collection of components that together perform a specified function, such as filter or treat water or prepare a batch of dialysate. The components in the "module" need not and often will not be housed in a discrete enclosure.

Further, as noted above, the invention may be practiced in a batch peritoneal dialysis embodiment in accordance with the principles described above. A vessel analogous to the ultrafiltration tank may be provided in fluid communication with the dialysate circuit for storing the volume of water to be introduced to the dialysate flow path. Alternatively, the water may be introduced directly into the dialysate without using a tank. The true scope and spirit of present invention is defined by the appended claims, interpreted in light of the foregoing.

We claim:

1. A method of adjusting the conductivity of a batch of dialysate in a dialysis machine, said machine having a substantially noncompliant, closed volume dialysate solution flow path comprising a dialysate solution tank for storing said batch of dialysate and a dialysate circuit conducting said dialysate from said dialysate solution tank to a dialyzer, said dialysate solution flow path having a predetermined estimated volume, comprising the steps of:

opening one or more batch chemical vessels containing concentrated dialysate solution chemicals and introducing substantially the entire contents of said concentrated dialysate solution chemicals to said tank, said entire contents of said concentrated dialysate solution chemicals in said batch chemical vessels intentionally overfilled in excess of the amount required to prepare a batch of dialysate at a predetermined desired conductivity level, said predetermined desired conductivity level associated with a dialysis prescription for a patient being dialyzed by said machine;

thereafter mixing said dialysate solution chemicals with water to form a dialysate solution;

measuring the conductivity of said dialysate solution;

calculating, from said measured conductivity, predetermined estimated volume and predetermined desired conductivity level, a volume of water needed to be added to said dialysate solution to dilute said dialysate solution to at least approximate said predetermined desired conductivity level;

introducing said volume of water into said dialysate solution flow path;

mixing said volume of water with said dialysate solution to thereby dilute said dialysate solution and lower the conductivity of said dialysate solution to said predetermined desired conductivity level, and subsequently draining a quantity of said dialysate solution from said dialysate solution flow path.

2. The method of claim 1, wherein said dialyzer is connected to an arterial line and a venous line, and wherein said step of draining comprises the step of flushing dialysate solution through said dialyzer into said arterial and venous lines connected to said dialyzer and out of said arterial and venous lines into a drain, said step of draining performed prior to a conducting a dialysis session using said dialysate solution.

3. The method of claim 1, wherein said dialysis machine further comprises an extracorporeal circuit having an arterial line and a venous line connected to said dialyzer, and wherein said step of draining comprises the steps of:

pumping said quantity of dialysate solution into said arterial line;

circulating said quantity of dialysate solution through the arterial line and a blood side of said dialyzer and through said venous line; and directing said dialysate solution from said venous line to a drain;

said steps of pumping, circulating and directing performed prior to conducting a dialysis session using said dialysate solution.

4. A method of adjusting the conductivity of a batch of dialysate in a dialysis machine, said machine having a dialysate solution flow path comprising a dialysate solution tank and a dialysate circuit conducting said dialysate from said dialysate solution tank to a dialyzer, said dialysate solution flow path having a predetermined estimated volume, comprising the steps of:

introducing concentrated dialysate solution chemicals to said tank in excess of the amount required to prepare a batch of dialysate at a predetermined desired conductivity level, said predetermined desired conductivity level associated with a dialysis prescription for a patient being dialyzed by said machine;

mixing said dialysate solution chemicals with water to form a dialysate solution;

measuring the conductivity of said dialysate solution;

calculating, from said measured conductivity, predetermined estimated volume and predetermined desired conductivity level, a volume of water needed to be added to said dialysate solution to dilute said dialysate solution to at least approximate said predetermined desired conductivity level;

introducing said volume of water into said dialysate solution flow path; and mixing said volume of water with said dialysate solution to thereby dilute said dialysate solution and lower the conductivity of said dialysate solution to said predetermined desired conductivity level;

wherein said dialysis machine further comprises an ultrafiltration tank in fluid communication with said dialysate solution flow path, and wherein said step of introducing said volume of water into said dialysate solution in accordance with said calculation comprises the step of supplying said volume of water to said ultrafiltration tank and directing said dialysate solution through said ultrafiltration tank.

5. Apparatus for adjusting the conductivity of a batch of dialysate, comprising:

a dialysis machine, said machine having a dialysate solution flow path comprising a dialysate solution tank and a dialysate circuit conducting said dialysate solution from said dialysate solution tank to a dialyzer, said dialysate solution flow path having a predetermined estimated volume, said dialysate solution made from a mixture of water with concentrated dialysate solution chemicals in a quantity in excess of the amount required to generate a batch of dialysate to a predetermined desired conductivity level for said predetermined estimated volume, said predetermined desired conductivity level associated with a dialysis prescription for a patient being dialyzed by said dialysis machine, said dialysis machine further comprising:

a conductivity sensor in said dialysate solution flow path measuring the conductivity of said dialysate solution;

a control system calculating from said measured conductivity, predetermined estimated volume and a predetermined desired conductivity level for said dialysate solution a volume of water needed to be added to said dialysate solution flow path to dilute said dialysate solution to at least approximate said predetermined desired conductivity level;

a water preparation circuit in fluid communication with said dialysate solution flow path, responsive to said control system, for introducing said volume of water into said dialysate solution flow path in accordance with said calculation, wherein said dialysate solution flow path further comprises a pump operative to mix said volume of water with said dialysate solution to thereby lower the conductivity of said dialysate solution to said predetermined conductivity level;

wherein said dialysis machine further comprises an ultrafiltration tank in fluid communication with said dialysate solution flow path, and wherein said volume of water is directed into said ultrafiltration tank and thereafter mixed with said dialysate solution.

* * * * *